US00PP10187P

United States Patent [19]

Yaneshita et al.

[11] Patent Number: Plant 10,187

[45] Date of Patent: Jan. 6, 1998

[54] 'MIYAKO' ZOYSIAGRASS

[76] Inventors: Makoto Yaneshita; Renri Nagasawa, both of 3-6-2, Akanehama, Narashino-shi, Chiba, 275, Japan

[21] Appl. No.: 615,955

[22] Filed: Mar. 14, 1996

[51] Int. Cl.[6] ..... A01H 5/00

[52] U.S. Cl. ..... Plt./90

[58] Field of Search ..... Plt./90

[56] References Cited

PUBLICATIONS

Anon. (GTITM UPOVROM listing) "Miyako" proposed May 13,1992.

*Primary Examiner*—James H. Feyrer

*Attorney, Agent, or Firm*—M. C. Engelke

[57] ABSTRACT

A new and distinct cultivar of an asexually reproduced zoysiagrass, *Zoysia japonica,* with a unique combination of characters including fall color retention, tolerance to Rhizoctonia large patch, having aggressive spread by stolons with long internodes and a distinct DNA fingerprint.

4 Drawing Sheets

BACKGROUND OF THE INVENTION

Filed of the Invention

The present invention relates to a new and distinct asexually reproduced variety of perennial zoysiagrass (*Zoysia japonica* (L)).

BRIEF SUMMARY OF INVENTION

This invention relates to a new and distinct perennial zoysiagrass plant, tested as 'Miyako', that was discovered by the inventors in a mowed, cultivated turf areas in the Southwestern islands of Japan. It was identified as a clone superior in rate of spread to the surrounding zoysiagrasses. 'Miyako' is an aggressively spreading cultivar, with adaption to sports fields, turf racetracks, industrial parks, and highway rights a ways, wherever zoysiagrass is adapted.

For purpose of registration under the "International Convention for the Protection of New Varieties of Plants" (generally known by its French acronym as the UPOV Convention) and noting Section 1612 of the Manual of Patent Examining Procedure, it is proposed that the new variety of zoysiagrass of the present invention be named 'Miyako' Zoysiagrass.

BRIEF DESCRIPTIONS OF THE ILLUSTRATIONS

DETAILED DESCRIPTION OF THE PLANT

Figure 1:
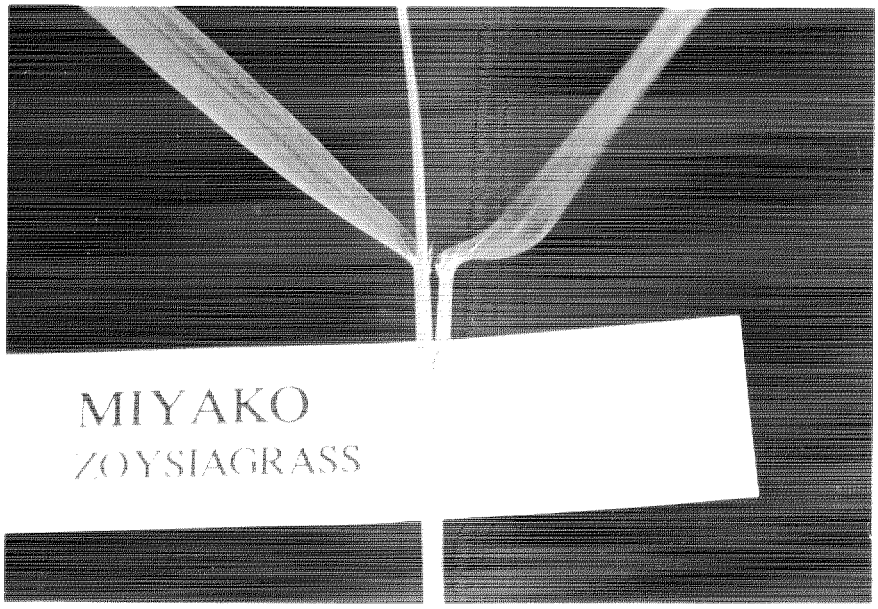
FIG. 1 is a photograph of the leaf blade and ligule of Miyako.
Figure 2:
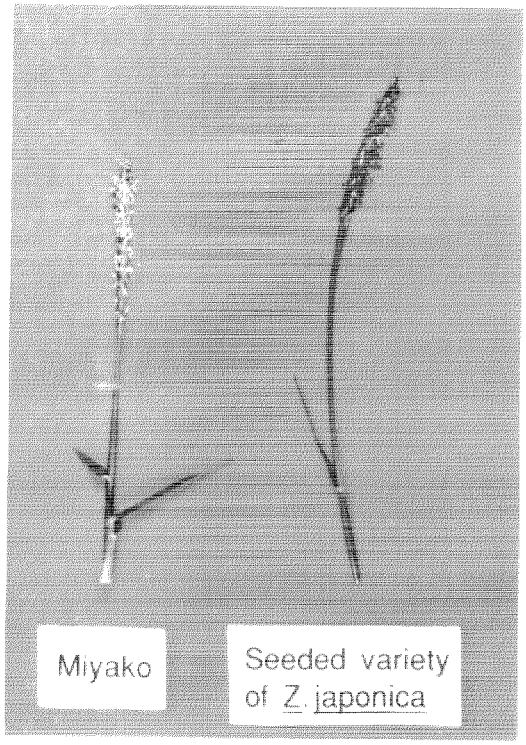
FIG. 2 is a photograph of the inflorescence of 'Miyako.'

'Miyako' was characterized in greenhouse and field conditions. 'Miyako' is a unique variety of zoysiagrass (*Zoysia japonica* Steud.). 'Miyako' was discovered under cultivated conditions described above in Japan and tested in field plots for three years at the same location. 'Miyako' was identified as more rapid in spread than the surrounding zoysiagrass and had a longer period of fall color retention than the surrounding zoysiagrasses. Based on DNA fingerprinting, 'Miyako' appears to be an interspecific hybrid between *Z. japonica* and *Z. matrella*. 'Miyako' was propagated by cutting of stolons, rooting them in soil, and planting of the rooted stolons to provide planting stock for studying performance and for comparison with commercial varieties. 'Miyako' remained stable in both performance and morphological characters after propagation. 'Miyako' has been propagated by sod, plugs, and stolons. Seed reproduction with self-fertility is not common in the *Zoysia* sp. No seedling establishment from 'Miyako' has been noticed in either greenhouse or field studies.

'Miyako' is distinguished from other varieties of zoysiagrass by the combination of characters of tolerance to Japanese strains of Rhizoctonia large patch, aggressive spread and fall color retention. 'Miyako' is closest in appearance and performance to 'El Toro' zoysiagrass.

'Miyako' has both rhizome and stolon growth. The stolons of 'Miyako' are aggressive in their spreading ability (Table 1), as illustrated by the internode length. The internode diameter is slender compared to 'El Toro' and 'Meyer' (Table 1). The stolons of 'Miyako' root adventitiously at the nodes. Color notations of plant tissues were based on the Munsell *Color Charts for Plant Tissues,* Munsell Color, Baltimore, MD, 1977. Light quality, photoperiod, and general growth of the plant affect color notations.

Leaf blades of 'Miyako' are rolled in the bud, are flat and stiff. The leaf blade length of 'Miyako' varies by growth conditions, but the third youngest leaf is 3.5 mm wide and 103.9 mm long, longer than both 'El Toro' and 'Meyer' when held under a 14 hour day length in growth chamber studies. There are hairs on the adaxial leaf surface of 'Miyako'. Measured under growth chamber conditions in October 1995, the genetic, adaxial leaf color of 'Miyako' is 2.5GY 6/4, with 'El Toro' having a leaf color of 2.5GY 5/2, and 'Meyer' having a color of 2.5G 3/4. The internode color of 'Miyako' is 5R 3/2.

The ligule of 'Miyako' is a ring of hairs, with the longest hairs approximately 4.3 mm in length. 'Miyako' has purple anthers and white stigmas, undistinguished in color from other plants of the species. The inflorescence of 'Miyako' is a terminal spike-like raceme, with spikelets on short pedicels. When grown in Japan in field trails in May 1994, 'Miyako' had a mean culm length of 9.0 cm, a floral region of 5.4 cm, with a mean of 46 florets per raceme, 2.8 mm in length. In trails in Japan, 'Miyako' showed a rating of 7 raceme number per unit area, with Korean Common having a rating of 5, when rated on a scale of 1–9 with 9=most racemes per unit area.

The chromosome number of 'Miyako' is 40.

In trials in Japan, 'Miyako' has shown turf quality data that includes color (rated on a scale of 1–9, where 9=darkest green) where Miyako had a rating of 5 where seeded Korean common had a rating of 7. In fall growth ratings, 'Miyako' had a rating of 8 where Korean common had a rating of 5, on a scale of 1–9 where 9=high growth rate. In spring greenup, 'Miyako' had a rating of 3 where Korean common had a rating of 6 when rated on a scale of 1 to 9, where 1=earliest spring greenup. In winter dormancy ratings, 'Miyako' had a rating of 8 with Korean Common rating 5, on a scale of 1–9, with 9=late dormancy.

Compared to other *Z. japonicas*, CM 15 has leaf blades longer and wider than 'El Toro' (U.S. Plant Pat. No. 5845) and 'Meyer'. CM 15 has white stigmas and purple anthers, in contrast to the pale yellow green stigma and anthers of ZT-26 (U.S. Plant Pat. No. 6,345) and the pale yellow colored anthers of ZT-4 (U.S. Plant Pat. No. 6,516): ZT-11 (U.S. Plant Pat. No. 7,074) reports few seed heads per unit area, whereas CM 15 reports a production rating of 7, when rated on a scale of 1–9, with 9=most.

'Miyako' has a distinctly different DNA fingerprint from (FIGS. 3 and 4) 'El Toro,' 'Meyer,' 'DALZ8512', 'DALZ8514', Common seeded *Z. japonica*, and 'Emerald.'

In comparison to 'Meyer' zoysiagrass, 'Miyako' is more aggressive in rate of spread and general growth, and has a more open and prostrate growth habit. 'Miyako' develops less thatch than 'Meyer' and retains green color longer in the fall. 'Miyako' has a smaller diameter node than either 'Meyer' or 'El Toro' but has longer internode than 'El Toro' and 'Meyer'. 'Miyako' has a wider and longer leaf than either 'Meyer' or 'El Toro' zoysiagrass. 'Miyako's' leaf length is four times longer and twice as wide as 'Emerald's,' and twice as long but similar in width as 'Meyer's' leaf. 'Miyako's' shade tolerance is less than 'Meyer' or 'Emerald' but has superior drought tolerance to either.

TABLE 1

Internode length as measured between the second and third nodes, internode diameter of the third internode, and node diameter of the third node measured on zoysiagrass plants. Plants were growing in a growth chamber with a 14-hour daylength, March 1995.

| Genotype | Internode length mm | Internode diameter mm | Node diameter mm |
|---|---|---|---|
| 'Miyako' | 43.3a* | 0.71bc | 1.03bc |
| 'El Toro' | 39.8ab | 0.94ab | 1.45abc |
| 'Meyer' | 24.1bc | 1.03a | 1.99a |

*Analysis of variance by General Linear Models, with means followed by the same letter not significantly different using Tukey's Studentized Range (HSD), alpha = 0.05. Only selected means presented.

TABLE 2

Leaf blade width and length measured on the third youngest leaf of zoysiagrasses. Plants were growing in a growth chamber with a 14-hour daylength, March 1995.

| Genotype | Blade width mm | Blade length mm |
|---|---|---|
| 'Miyako' | 3.52a* | 119.2a |
| 'El Toro' | 3.26abc | 68.3b |
| 'Meyer' | 2.59c | 74.3b |

*Analysis of variance by General Linear Models, with means followed by the same letternot significantly different using Tukey's Studentized Range (HSD), alpha = 0.05. Only selected means presented.

Detailed Summary of DNA Fingerprinting Analysis

Figure 3:
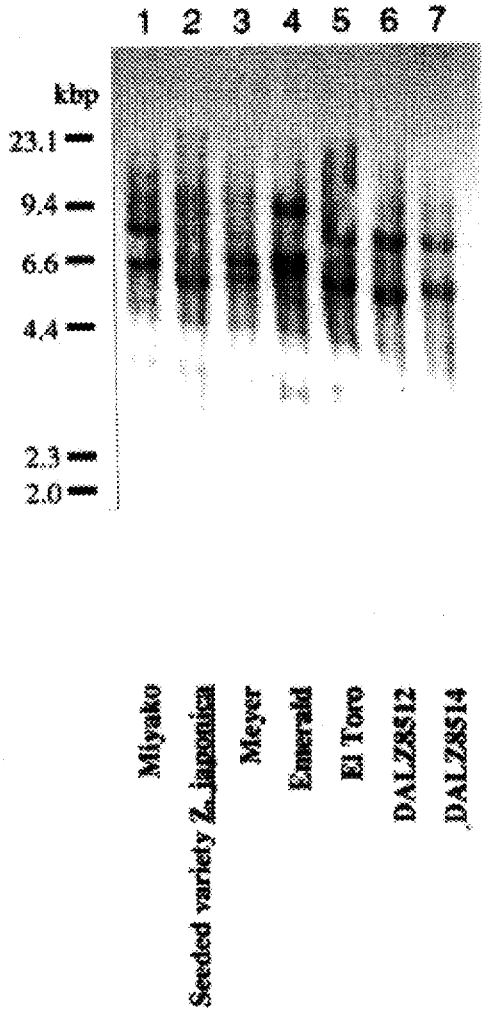
FIGS. 3 and 4 are DNA fingerprints of 'Miyako' produced by RFLP.

Mr. Yaneshita of Japan Turfgrass, Inc. performed the DNA fingerprint analysis. The zoysiagrass fingerprints were of 'Miyako,' a seeded variety of common *Z. japonica*, 'Meyer,' 'Emerald,' 'El Toro,' DALZ8512, and DALZ8514. The RFLP hybridization patterns are with the ZG7 clone. Total DNA's extracted from mature leaves of materials were digest with HindIII. Restriction fragments were transferred onto a nylon-membrane after Southern blotting. Labeling ZG7 clone and detection of hybridization were conducted by ECL system produced from Amersham Ltd. 'Miyako' is identified by a unique fragment of 6.0 kbp from other varieties (FIG. 3).

Figure 4:
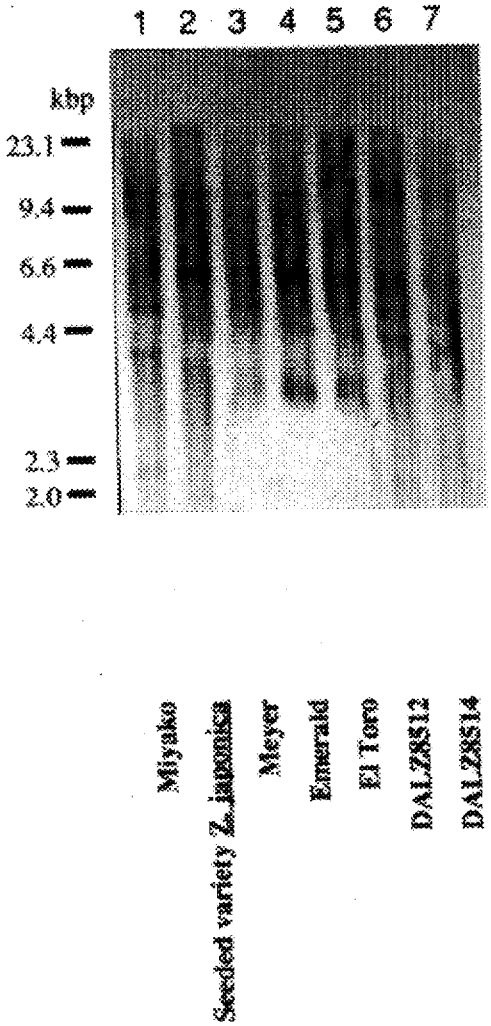

'Miyako' identified by a unique fragment of 3.5kbp from a seeded variety of common *Z. japonica*, 'Meyer,' 'Emerald,' 'El Toro,' DALZ8512, and DALZ8514 (FIG. 4).

I claim:

1. A new and distinct cultivar of an asexually reproduced zoysiagrass, *Zoysia japonica* plant, as described and illustrated herein, having a unique combination of characters including fall color retention, tolerance to Rhizoctonia large patch, having aggressive spread by stolons with long internodes, and a distinct DNA fingerprint.

* * * * *